United States Patent [19]

Ackerman

[11] Patent Number: 4,716,896
[45] Date of Patent: Jan. 5, 1988

[54] BRONCHIAL CATHETER

[75] Inventor: Bernard Ackerman, Metuchen, N.J.

[73] Assignee: Ackrad Laboratories, Cranford, N.J.

[21] Appl. No.: 892,792

[22] Filed: Aug. 1, 1986

[51] Int. Cl.⁴ .............................................. A61M 16/00
[52] U.S. Cl. ............................ 128/200.26; 128/207.14
[58] Field of Search ....................... 128/200.26, 207.14, 128/207.15, 207.16, 207.17; 604/119

[56] References Cited

U.S. PATENT DOCUMENTS

| | | | |
|---|---|---|---|
| 3,039,463 | 6/1962 | Dickey, Jr. et al. | 604/119 |
| 3,375,828 | 4/1968 | Sheridan | 604/119 |
| 3,538,918 | 11/1970 | Engelsher | 128/200.26 |
| 4,502,482 | 3/1985 | DeLuccia et al. | 128/207.15 |
| 4,512,765 | 4/1985 | Muto | 604/119 |

FOREIGN PATENT DOCUMENTS 2096467 10/1982 United Kingdom ........... 128/207.15

*Primary Examiner*—Edward M. Coven
*Assistant Examiner*—J. P. Lacyk

*Attorney, Agent, or Firm*—Lackenbach Siegel Marzullo & Aronson

[57] ABSTRACT

A system for positioning a catheter in the left bronchus of a patient, who is undergoing a medical procedure with an endotracheal tube to control the patient's breathing. The catheter tube is shaped in a concave curve and is semi-rigid and capable of being biased. The endotracheal tube is shaped in a concave curve in a plane generally aligned in the left-right bisecting plane of the body of the patient. A bronchial curved portion of the catheter extends outwardly from the bottom area of the catheter tube at an angle from the bisecting plane toward the left bronchus. The curved catheter aligns with the curvature of the endotracheal tube during the insertion process and the bronchial curved portion automatically aligns with the left main-stem bronchus. Further insertion results in the final positioning of the distal end of the catheter in the left bronchus. The catheter can be used for either evacuation of mucous or for the injection of a fluid, such as a mucous thinner. The catheter may also be inserted into a curved tracheotomy tube used in a tracheotomy procedure.

2 Claims, 6 Drawing Figures

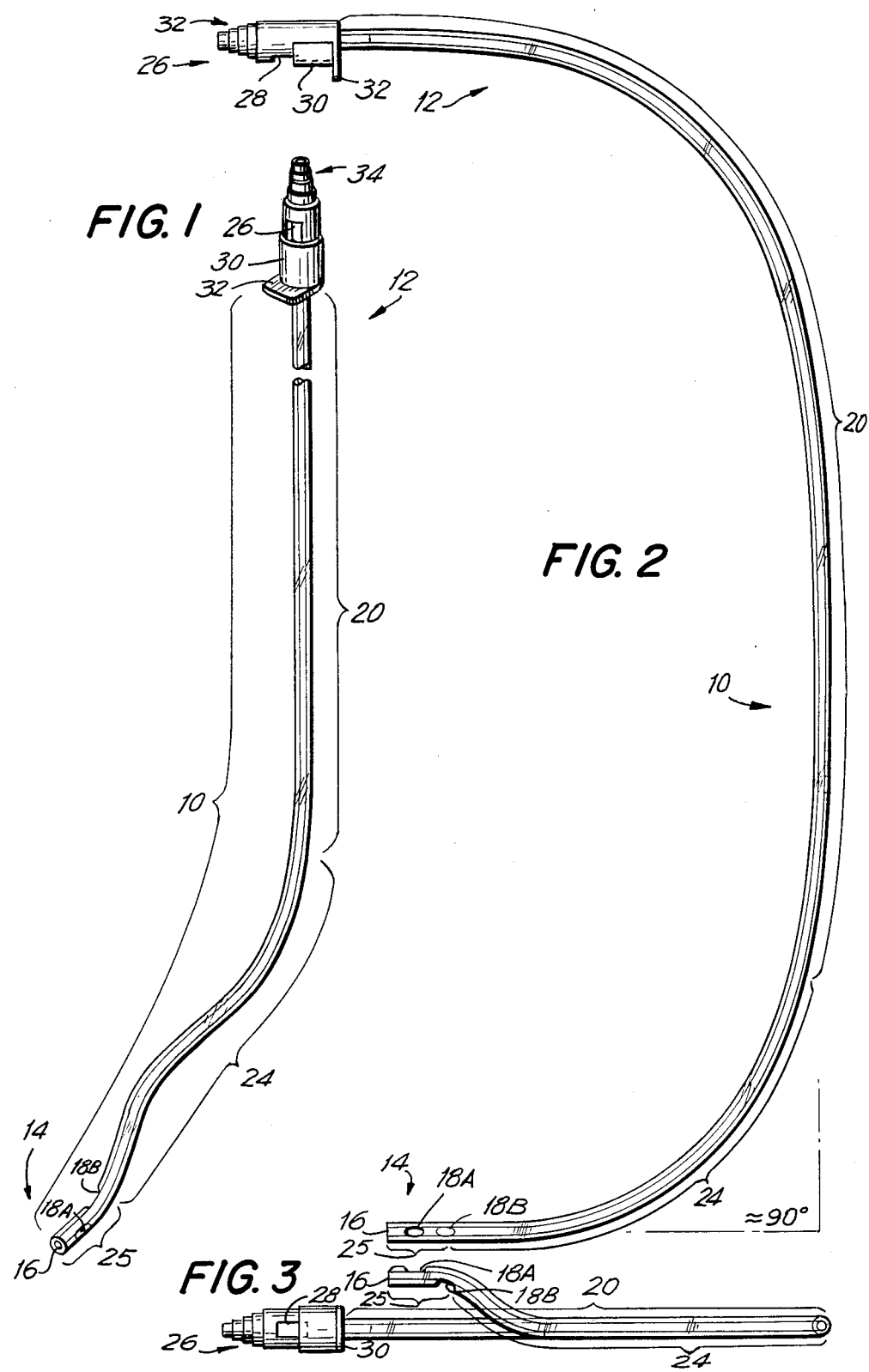

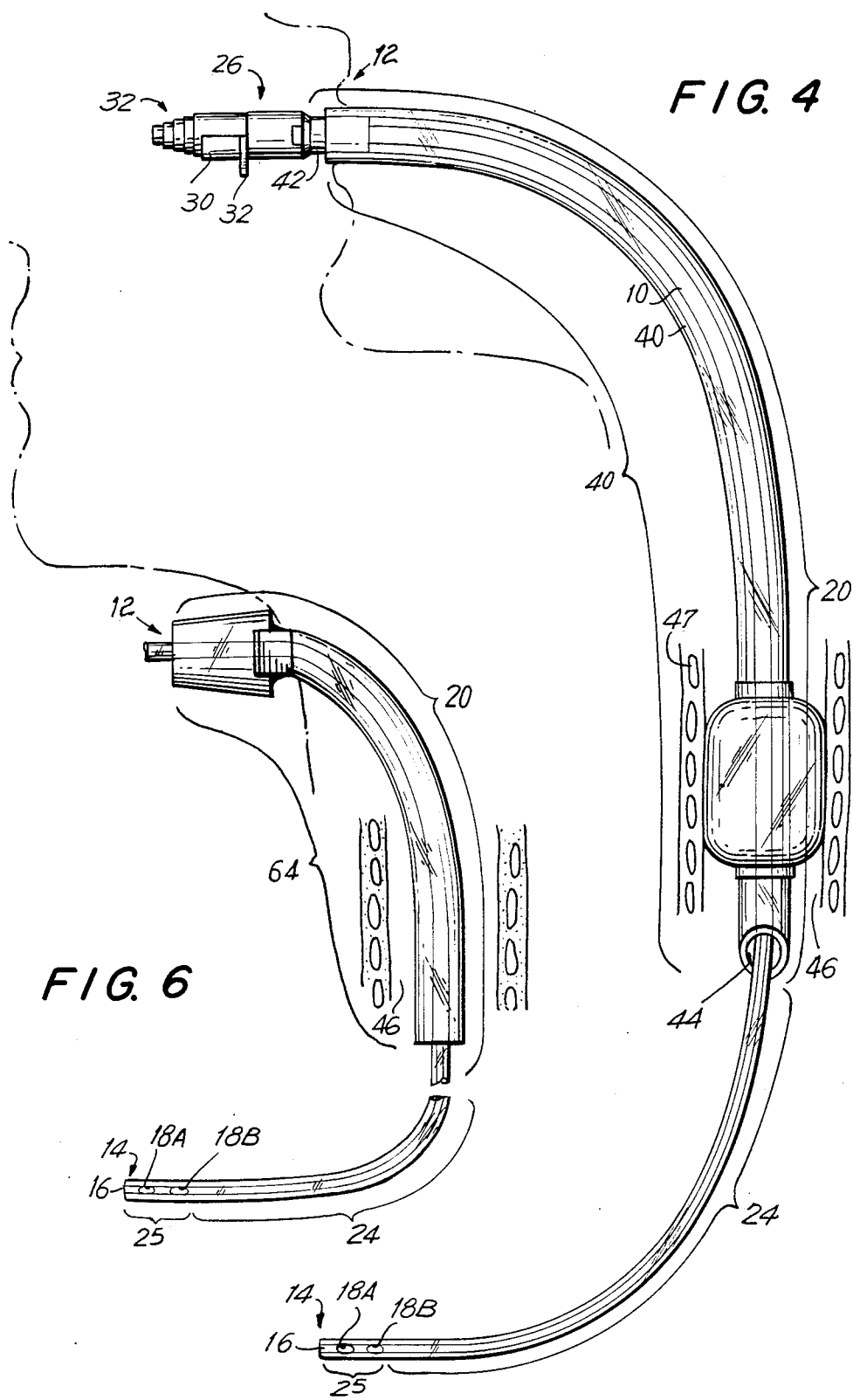

BRONCHIAL CATHETER

This invention relates to catheters and in particular to a catheter that is adapted to be rapidly directed to the left bronchus of a patient.

BACKGROUND OF THE INVENTION

A standard medical procedure is to insert an endotracheal tube into the the trachea of a patient to control the patient's breathing. When mucous interferes with breathing, a suction catheter connected to a vacuum apparatus is inserted through the endotracheal tube into the trachea, and, if necessary, into the left and right bronchi one bronchus at a time for removal of the mucous. It is important that this procedure be performed as efficiently and rapidly as possible.

The left main-stem bronchus presents a special access problem to a person who is inserting a suction catheter into a patient. Humans have left and right bronchial main-stem passages branching at slight angles from the trachea. The left bronchial passage is more difficult to reach than the right bronchial passage because it is slightly smaller and branches at a slightly greater angle from the main trachea than the right bronchial passage. Curved-tip catheters have been used to reach the bronchial passages and in particular the left bronchial passage. Such catheters are somewhat more likely to gain access to gain access to the left passage than straight-tip catheters, which have little or no chance of success. Problems arise, however, because it is often difficult to know where the curved tip is pointing and such curved tip catheters end up in the right bronchial passage as often as 50% of the time. When the catheter is to be positioned in each lung for drainage, the patient is turned over in turn on each side which is to be drained so as to use gravity to aid in a downward movement of the tip of the catheter. The carina, the "cough center" positioned at the junction of the left and right bronchi, is particularly sensitive to touching and should be avoided during the insertion procedure.

A catheter is inserted into a bronchus generally to suck out mucous, a procedure that is often performed during the time a patient is on a ventilator apparatus. Rapid access to the difficult left bronchus results in less time off the ventilator. The net result of rapid access can lead to a shorter stay in a critical care unit.

The same catheter tube that is used to suck mucous from a bronchus can be used at times to move liquid into the bronchus in order to thin the mucous prior to suctioning. Also, a medication can be placed in the bronchus through the catheter tube.

It is an object of this invention to provide a suction catheter that can be easily and rapidly placed into the left bronchus.

It is still another object of this invention to provide a catheter that is adapted to be easily directed into the left bronchial passage and that is further adapted to be used both for suctioning or injecting purposes.

SUMMARY OF THE INVENTION

Accordingly, in order to meet the above objects, a catheter system adapted for insertion into one of the bronchial passages of a patient is provided that includes an endotracheal tube positioned in the tracheal passage having an open end external to the body and an open internal end located in the trachea proximal to the left and right bronchial passages of the patient. A catheter tube adapted to be positioned in the endotracheal tube has a proximal end to be positioned outside the patient and a distal end to be located in the left bronchus of the patient. The endotracheal tube has a concave configuration as required by the structure of the trachea and in order to facilitate entry into the trachea. The flexible, but also semi-rigid, catheter also has a concavely curved configuration that is adapted to align itself with the concavely curved endotracheal tube upon insertion into the endotracheal tube. The concavely curved catheter tube becomes aligned with the concavely curved endotracheal tube along the left-right bisecting plane of the patient. A bronchial curved tube portion of the catheter extends outwardly from the lower end of the lower portion of the catheter from the bisecting plane in the direction of the left bronchial passage into which it is to be placed. The catheter tube is made of a material that if required can transmit torque from the proximal end to the distal end so that the distal end can be maneuvered during the insertion process in the event of fine maneuvering. A connector to a vacuum source preferably includes a vent that is used to control the strength of the vacuum force. The vent is adapted to be aligned with the bisecting plane so that a user is aided in aligning the distal end of the catheter into the stem of the left bronchus. The catheter can also be used to inject fluids into the bronchus.

The catheter described above may also be inserted into a concavely curved tracheotomy tube which is short as compared with the endotracheal tube described above and is inserted through the throat of the patient. The catheter likewise automatically positions itself in the left bronchial catheter in accordance with its self-alignment with the curve of the tracheotomy tube.

DESCRIPTION OF THE DRAWINGS

FIG. 1 is a fragmented perspective view of the catheter of the present invention prior to insertion into the left bronchial passage of a patient with the upper portion of the catheter generally straight;

FIG. 2 is a side elevational view of the catheter shown in its natural state prior to use;

FIG. 3 is a bottom view of the catheter shown in FIG. 2;

FIG. 4 is a side view of the catheter inserted into an endotracheal tube as it would be positioned in the trachea and left bronchial passage (not shown) of a patient;

FIG. 6 is a side view of the catheter inserted into a tracheotomy tube as it would be positioned in the trachea and left bronchial passage (not shown) of a patient.

DETAILED DESCRIPTION OF THE INVENTION

Figure 5:
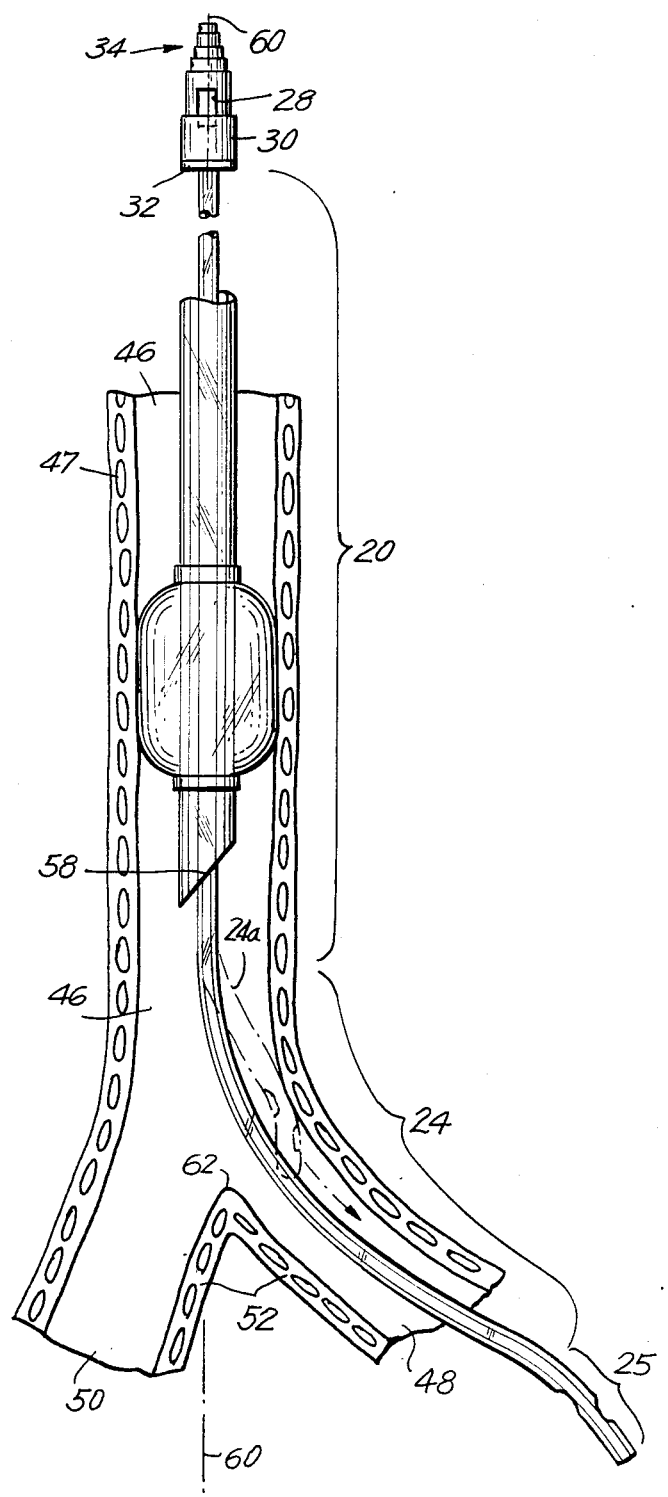
FIG. 5 is a frontal view of the catheter and endotracheal tube positioned in the left bronchial passage of a patient with one position of the movement of the catheter into the left bronchial passage shown in phantom line.

Reference is now made in detail to the drawings where the same numerals indicate the same or similar elements.

An elongated catheter tube 10 shown prior to use in perspective in FIG. 1 and in side and bottom views in FIGS. 2 and 3 has a proximal end 12 positioned external to the body of a patient and a distal end 14 adapted to be located in the bronchus of the patient. Catheter 10 is adapted to pass fluids from the bronchus. Distal end 14 has an end aperture 16 and a pair of side apertures 18A and 18B located proximal to distal end 14 and preferably positioned on opposite sides of the catheter. End aperture 16 is optional and can be eliminated in certain types of patients, for example, children. Catheter 10 includes an upper concavely curved tube portion 20 extending from proximal end 12, a bronchial curved portion 24 extending from the inner end of concavely curved tube portion 20 adapted to be positioned in the left bronchus of the patient, and a curved tip portion 25 extending from bronchial curved tube portion 24 to distal end 14. Upper tube portion 20 is shown artificially straightened in FIG. 1 for purposes of exposition and shown concavely curved in FIGS. 2 and 3 in the position it naturally assumes prior to insertion into the tracheal tube.

A cylindrical transition connector member 26 forming a tubular passage is attached via a male connector to proximal end 12 at one end and is adapted to be connected to a fluid collector (not shown) and a vacuum pump (not shown) at the other end. Connector 26 has an optional controlling device that includes a side vent 28 that opens to the internal tubular passage. A partially cylindrical cover member 30 mounted to the outside of connector is slidably movable axially relative to connector 26 over a plurality of positions relative to side vent 28 between a first position wherein side vent 28 is fully open and a second position wherein side vent 28 is fully closed. The position of cover member 30 shown in FIGS. 1-13 is in a partially open mode. Cover member 30 includes an external tab 32 that is adapted to be moved by a thumb so as to slide cover member 30 relative to side vent 28; and further includes an internal stop tab (not shown) that is adapted to lock against the bottom edge of side vent 28 when cover member 30 has completely uncovered the side passage. The strength of the pull of the suction in catheter 10 can be selectively controlled by the size of side vent 28. A series of concentric cylindrical steps 34 of decreasing diameter extend upwards from the side opposite proximal end 12 so as to provide a selective series of male connecting members for attachment to the connecting tube leading to the collector and the vacuum pump.

Catheter tube 10 is shown in its mounted position in FIGS. 4 and 5 positioned in an endotracheal tube 40, which has an open external end 42 located outside the patient and an open internal end 44 located in the tracheal passage 46 formed by the tracheal wall 47 and spaced generally proximally above the left and right main-stem bronchial passages 48 and 50, respectively. The bronchial passages are formed by the bronchial walls 52. Endotracheal tube 40 extends from external end 42 into the bottom area of tracheal passage 46 at internal end 44. Internal end 44 of endotracheal tube 40 is cut at an angle 58 that opens toward left bronchus 48. Endotracheal tube 40 is semi-rigid and is biasable from its concavely curved configuration in its free state so as to conform with the throat and trachea of the patient.

Endotracheal tube 40 is first inserted into the patient's tracheal passage 46 and attached to a ventilator apparatus, which is removed prior to the insertion of catheter tube 10 into endotracheal tube 40. The initial insertion of endotracheal tube 40 into tracheal passage 46 results in endotracheal tube 40 forming lower a concavely curved configuration in accordance with the structure of the particular human trachea into which it is inserted. The term concave is used here to indicate the orientation of the tracheal curve relative the front side of the chest area, that is, the trachea is configured in a long curve towards the rear side of the body. FIG. 4 indicates this curve ideally, since endotracheal tube 40 and catheter 10 are shown positioned generally as they would be if they were mounted in the tracheobronchial passage. Endotracheal tube 40 is generally aligned with an imaginary bisecting plane 60 of the patient's body as indicated in FIG. 5.

Catheter 10 is made of a semi-rigid, somewhat flexible plastic material that has biasable qualities in that it will return to its original shape prior to its insertion into endotracheal tube 40. This original shape is shown in FIGS. 2-3. Therefore, as catheter 10 is moved down endotracheal tube 40, it will align itself with the concavely curved endotracheal tube in alignment with bisecting plane 60. In turn, bronchial curved portion 24, which generally retains its relationship with upper curved portion 20, will extend outwardly from plane 60 towards left bronchial passage 48, the passage for which catheter 10 is structured to enter during the insertion procedure. Bronchial curved portion 24 is shown in FIG. 5 in phantom line automatically aligning itself with left bronchial passage 48 during the insertion process. Curved portion 24 is biased upwardly away from the carina 62 at the junction of left and right bronchi 48 and 50, so that the chance of irritation of the carina is avoided.

Curved tip portion 25 is oriented in general alignment with plane 60 as shown in FIG. 3, which illustrates catheter 10 in a bottom view. The outer edge of curved tip portion 25 presses against the inner surface of bronchial wall 52 during insertion. Angle 58 faces left bronchus 48 and aids in the directing of bronchial curved portion 24 into left bronchial passage 48.

Catheter tube 10 is flexible enough so as to adapt itself to the changing configurations of endotracheal tube 40 and to the left bronchial passage 48 during the entering process, but at the same time it is sufficiently self-biased to return to its original shape as shown in FIGS. 2 and 3 when the constraints forcing it out of its original shape are removed. Also, catheter 10, which is a unitary member, is capable of transmitting force between the proximal and distal ends 12 and 14. Thus, if any minor problem arises during the insertion process, the user has the option of fine-maneuvering distal end 14 by application of torque at proximal end 12.

Side vent 28 of connector 26 is aligned with bisecting plane 60 so that a user can approximate the relative position of bronchial curved portion 24. This alignment mark is of aid to the user when applying torque to proximal end 12 during the insertion process in the event fine maneuvering is used.

Catheter 10 can be made of various plastic materials that meet the physical requirements set forth above. These plastic materials include, for example, polyolefins copolymerized with vinyl acetate; ethyl acrylate; and methyl acrylate.

Catheter 10 is adapted to be inserted into the bronchial cavity for the purpose of injecting the left bronchus with a fluid. Fluids that can be injected include a liquid adapted to thin the mucous and medication.

In certain procedures when time is of the essence a tracheotomy is performed and a short inner cannula, or tracheotomy tube, 64 is inserted through the skin into the tracheal passage 46 of a patient 66 as shown in FIG. 6. Tracheotomy tube 64 is concavely curved in a manner analogous to endotracheal tube 40. Catheter 10 is then inserted into the trachea and left bronchial passage 48 through tracheotomy tube 64. Catheter 10 self-aligns itself with the bisecting plane (not shown in FIG. 6) of the body as it is moved down concavely curved tracheotomy tube 64. Bronchial curved portion 24, which generally retains its relationship with tracheotomy tube 64, will extend outwardly from the bisecting plane towards left bronchial passage 48, which catheter 10 is structured to enter during the insertion procedure.

Catheter tube 10 is inserted into endotracheal tube 40, which has been placed in the trachea of the patient previously, as follows:

a. inserting distal end 14 of catheter tube 10 into external end 42 of endotracheal tube 40, which is already in place in the trachea of the patient;

b. advancing distal end 14 into endotracheal tube 40 so that concavely curved catheter tube 10 aligns with concavely curved endotracheal tube 40 along bisecting plane 60; at this time bronchial curved tube portion 24 presses against the inner surface of the outward side of endotracheal tube 40 then automatically extends into left bronchial passage 48 after emerging from internal end 44 of the endotracheal tube;

c. continue advancing catheter 10 until bronchial tube portion 24 is positioned in left bronchus 48 as needed;

Another possible step could include aligning distal end 14 during fine maneuvering by applying torque to proximal end 12. This step is aided by the user positioning distal end 14 by alignment of side vent 28 relative to bisecting plane 60.

Although the present invention has been described in some detail by way of illustration and example for purposes of clarity and understanding, it will, of course, be understood that various changes and modifications may be made with the form, details, and arrangements of the parts without departing from the scope of the invention as set forth in the following claims.

What is claimed is:

1. A bronchial catheter system for insertion of a catherter through an endotracheal tube positioned in the main tracheal passage of a patient and then into the left bronchial passage, comprising, in combination, a preformed endotracheal tube adapted to be positioned in the tracheal passage and having an open external end located outside the patient and an open internal end located in the trachea proximal to the left and right bronchial passages of the patient, tube means adapted to be positioned in the endotracheal tube and in the bronchial passage, said tube means having a proximal end adapted to be located outside the patient and a distal end adapted to be located in the left bronchial passage of the patient, said tube means defining a first tube section extending from said proximal end to a first joining portion extending from said proximal end; a second tube section joined to said first joining portion and extending to a second joining portion; and a third tube section extending from said second joining portion to said distal end, said tube means being for passing fluids between the left bronchus and said proximal end, said distal end having aperture means for passing the fluids between the left bronchus and said tube means, first positioning means associated with said first tube section for positioning said endotracheal tube in the trachea of the patient, said first tube section being precurved to extend from said proximal end to a first joining portion in a first plane, said first plane being aligned with the left-right bisecting plane of the body of the patient and having forward and rearward portions and upper and lower portions relative the body of the patient, said proximal end being positioned forwardly and upwardly and said joining portion being positioned at an area downwardly and generally between said forward and rearward portions, said first section forming a front to back tracheal curve between said proximal end and said first joining portion so as to accommodate to the tracheal curve of the treacheal passage of the body;

second positioning means associated with said second tube section for positioning said endotracheal tube in the left bronchus of the patient, said second tube portion being precurved to extend in a second plane oriented at a downward obtuse angle relative to said first plane extending from a transverse planar conjuction between said first and second planes so as to pass into the left tracheal passage upon insertion, said second tube section also simultaneously extending forwardly in said second plane so as to accommodate the bronchial curce of the bronchial passage, and third positioning means associated with said tube means for pressing against the top inner surface of the bronchial wall during insertion of the catherer into the left bronchial passage of the patient, said third tube section being precurved to extend in a third plane generally parallel to said first plane and forwardly relative to said second joining area.

2. The system according to claim 1, wherein said third tube section extends forwardly from said second joining area to said distal end in a plane generally normal to said first plane.

* * * * *